(12) United States Patent
Grotjahn et al.

(10) Patent No.: US 7,777,029 B2
(45) Date of Patent: Aug. 17, 2010

(54) BIFUNCTIONAL CHELATORS FOR SEQUESTERING LANTHANIDES

(75) Inventors: Douglas Grotjahn, San Diego, CA (US); Erik Wiener, Pittsburgh, PA (US)

(73) Assignee: San Diego State University (SDSU) Foundation, San Diego, CA (US)

( * ) Notice: Subject to any disclaimer, the term of this patent is extended or adjusted under 35 U.S.C. 154(b) by 0 days.

(21) Appl. No.: 11/743,654

(22) Filed: May 2, 2007

(65) Prior Publication Data

US 2008/0107606 A1    May 8, 2008

Related U.S. Application Data

(60) Provisional application No. 60/797,110, filed on May 2, 2006.

(51) Int. Cl.
*C07D 255/02* (2006.01)
*C07D 257/02* (2006.01)
*C07D 259/00* (2006.01)

(52) U.S. Cl. ..................................... 540/474

(58) Field of Classification Search .................. None
See application file for complete search history.

(56) References Cited

U.S. PATENT DOCUMENTS 6,180,113 B1 * 1/2001 Platzek et al. ............... 424/400
6,894,151 B2 * 5/2005 Platzek et al. ................. 534/16

* cited by examiner

*Primary Examiner*—James O Wilson
*Assistant Examiner*—Noble Jarrell
(74) *Attorney, Agent, or Firm*—Gavrilovich, Dodd & Lindsey; Gregory P. Einhorn

(57) ABSTRACT

The present invention relates to a method for preparing a bifunctional chelator for lanthanide. The method comprises the steps of providing a starting material which has an amino and carboxyl group; protecting the amino with an amino protecting group and the carboxyl with a carboxyl protecting group to produce a protected compound; reacting the protected compound with cyclen to generate a monoalkylated cyclen; reacting the monoalkylated cyclone with an activated compound to generated tetra-alkylated cyclone; removing the amino protecting group with a first protecting group removal reagent; and removing the carboxyl protecting groups with a second protecting group removal reagent to yield a bifunctional chelator having three more carboxyl groups and one or more amino groups.

2 Claims, 4 Drawing Sheets

(RRRR)-1  X = O, R³ = CH₃   DOTMA analog
(R)-2     X = O, R³ = H     DOMA analog
(RRRR)-3  X = H + H, R³ = CH₃   HP-DO3A analog

BIFUNCTIONAL CHELATORS FOR SEQUESTERING LANTHANIDES

CROSS REFERENCE TO RELATED APPLICATIONS

This application is a non-provisional application claiming benefit of priority under 35 U.S.C. §119(e) of U.S. Provisional Application Serial No: 60/797,110, filed May 2, 2006. The aforementioned application is explicitly incorporated herein by reference in its entirety and for all purposes.

STATEMENT AS TO FEDERALLY SPONSORED RESEARCH

This invention was made with Government support under a grant from National Institutes of Health, RO1 A145657-01. The United States Government may have certain rights in the invention.

TECHNICAL FIELD

The present invention relates to a method for synthesizing a bifunctional chelator for sequestering lanthanides.

BACKGROUND OF THE INVENTION

Magnetic resonance imaging ("MRI") for medical diagnostics can benefit tremendously from use of contrast agents, which are gadolinium compounds. DOTMA and DOTA are well-studied molecules capable of binding gadolinium ions ($Gd^{3+}$), forming very stable complexes. Each complex can bind a water molecule and alter its relaxivity and hence be used as a MRI contrast agent. The DOTMA complex is superior.

However, neither DOTMA not DOTA are bifunctional, that is, neither can be linked covalently to another molecule, meaning that they cannot be incorporated into polymers, attached to surfaces, or otherwise modified and targeted to a specific disease. There are a few bifunctional derivatives of DOTA in the literature but they are very tedious to make and even making 10 grams is difficult. The cost of buying such compounds can be thousands of dollars per gram.

The present invention provides a first bifunctional DOTMA analog and a robust synthetic method for preparing this analog. The synthetic method is scalable for readily producing 50-gram, 500 gram or more of the bifunctional DOTMA molecule. Moreover, this same chemistry is also applicable to make a related bifunctional DOTA and DO3A analogs as contrast agents with different properties.

SUMMARY OF THE INVENTION

In general, the bifunctional chelator of the present invention has a chelating moiety with specific geometry and charge, and a side arm with a functional group, such as hydroxyl, thiol, amino, hydrazine, or carbonyl, for attachment to a carrier, such as dendrimers, nanoparticles, and quantum dots. The chelating moiety may be any molecules which have sufficient binding affinity for a lanthanide including DOTMA (1), DOTA (2), HP-DO3A (3), or analogs or derivatives thereof DOTMA (1) and DOTA (2) each have four carboxylates whereas HP-DO3A (3) has three carboxylates and one hydroxyl group.

The present invention provides a method for preparing a bifunctional chelator for a lanthanide, which comprises the steps of providing a starting material which has an amino and carboxyl group; protecting the amino with an amino protecting group and the carboxyl with a carboxyl protecting group to produce a protected compound; reacting the protected compound with cyclen to generate a monoalkylated cyclen; reacting the monoalkylated cyclone with an activated compound to generated tetra-alkylated cyclone; removing the amino protecting group with a first protecting group removal reagent; and removing the carboxyl protecting groups with a second protecting group removal reagent to yield a bifunctional chelator having three more carboxyl groups and one or more amino groups.

In one aspect, compounds 1 and 2 are designed to have four free carboxylates and a highly nucleophilic primary aliphatic amino group for conjugation. The aliphatic amino group was expected to show greater nucleophilicity and attachment efficiency than does an aromatic amino group.[2]

In another aspect, amino acid esters are susceptible to base-catalyzed racemization. Because the products and intermediates containing the cyclen core are all bases, column chromatography on silica requires rather polar solvents containing base to minimize streaking. In order to avoid epimerization (which was actually encountered in development of the successful route), column chromatography was to be avoided. This simplifies and speeds the synthesis, particularly on large scale.

In yet another aspect, the chelating moiety is the (RRRR)-stereoisomer of DOTMA.[3] A diastereomeric mixture of products is a heterogeneous population. Enantiomerically pure precursors and reactions which preserve e.e. are chosen carefully throughout.

In still another aspect, ester and primary amine protecting groups are chosen in the synthesis to be removed under different conditions. The four carboxylic acids are designed to be protected as methyl esters for simpler NMR spectra and so that they are all removed with a single reagent. The present invention provides In further aspect, the organic synthetic method of the present invention is used to construct bifunctional molecules having one end for binding gadolinium tightly (a chelator) and other end being firmly and covalently attached to a nanodevice, such as a dendrimeric nanodevice. Without these properly designed bifunctional molecules, the nanodevice could fail for a number of reasons, including release of toxic gadolinium or lack of desired gadolinium-water interactions.

DETAILED DESCRIPTION OF THE INVENTION

As used in this disclosure, the singular forms "a", "an", and "the" may refer to plural articles unless specifically stated otherwise. Furthermore, the use of grammatical equivalents of articles such as "functionalization", "modification", or "derivatization" is not meant to imply differences among these terms unless specifically indicated in the context.

Unless defined otherwise, all technical and scientific terms used herein generally have the same meaning as commonly understood by one of ordinary skill in the art to which this invention belongs. Generally, the nomenclature used herein and the laboratory procedures in analytical chemistry, organic chemistry, material sciences, and nanotechnology described herein are those well known and commonly employed in the art. Standard techniques, or modifications thereof, are used for chemical syntheses and chemical analyses of the present invention (see generally, March, "ADVANCED ORGANIC CHEMISTRY: REACTIONS, MECHANISMS, AND STRUCTURE", 3rd ed. (1985) John Willey & Sons, New York, N.Y.)

Figure 2:
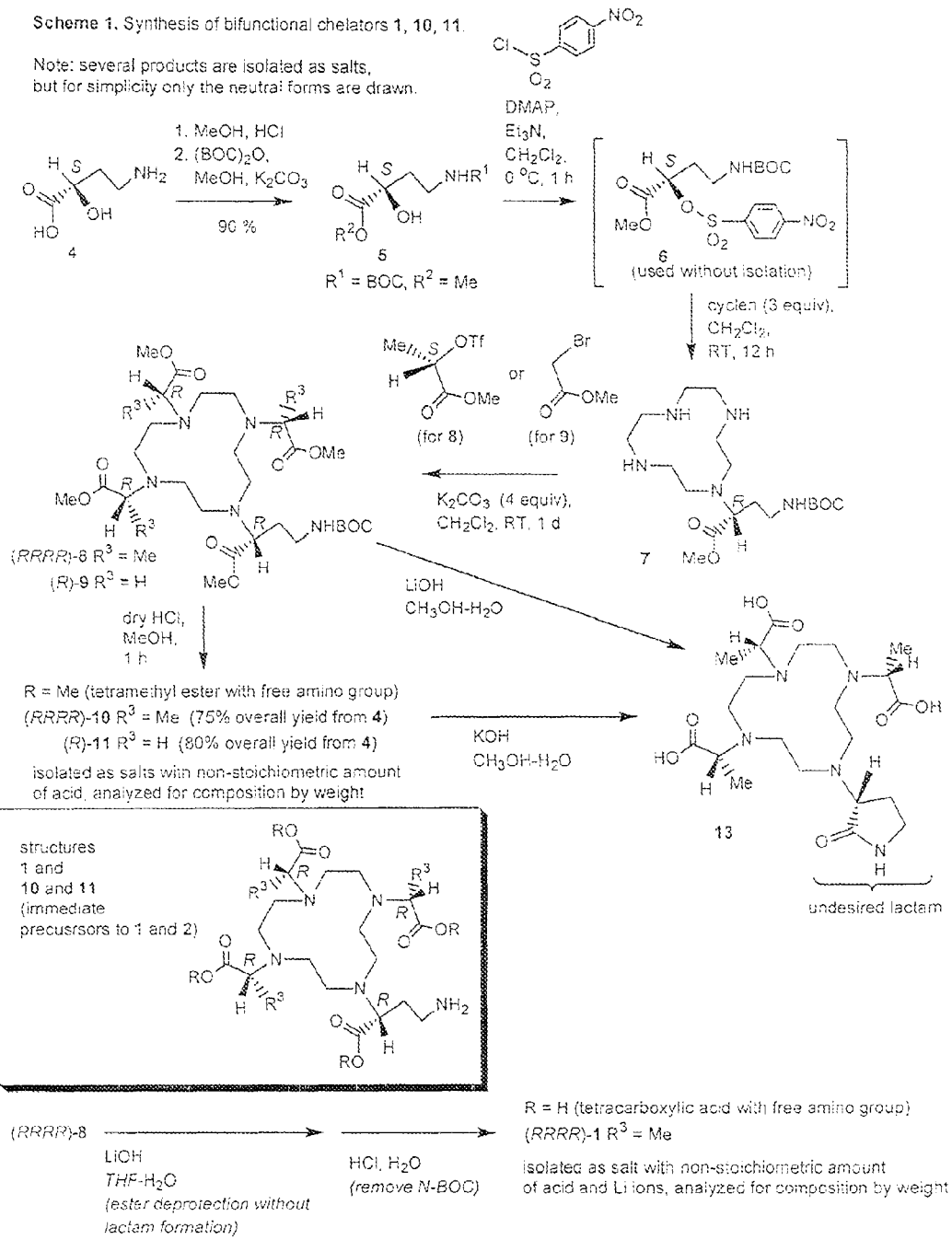
FIG. 2 is a representative scheme for the synthesis of bifunctional chelators for lanthanides.

The synthesis of the bifunctional chelator of the present invention is shown in FIG. 2. To start the synthesis, commercially available (S)-4-amino-2-hydroxybutyric acid 4 was protected with a methyl group for the carboxyl group and a BOC group for the amino group, to give 5 as oil in about 90% yield. Notably, the protected compound 5 was purified readily using silica gel chromatography. This reaction also produced a minor side-product (<5% yield) which has BOC groups on both the amine and hydroxyl groups. Other common protecting groups for both carboxyl and amino groups may also be used as described bar Green and Wuts (Protective Groups in Organic Synthesis, $3^{rd}$, John Wiley & Sons, New York). For example, Cbz may be used in the place of Boc and tert-butyl may be used in the place of methyl.

The next step involves the activation of the hydroxyl group of compound 5 for the alkylation of cyclen. In our early work, we found that the hydroxyl group of compounds such as 5 could be activated by conversion to a bromide (not shown), but that subsequent alkylation with cyclen was very slow, leading to partial racemization at the single chiral center.[4] Moreover, the methods available to make the bromide inverted the configuration at C-2, giving (R)-bromide and then the undesired (S) configuration of 7 after reaction with cyclen. Activation of the hydroxyl group as a mesylate solved the problem of double inversion, but the alkylation step was just as slow as when using the bromide. Attempts to activate the hydroxyl group as a triflate failed, because the triflate was so reactive that the carbamate group in BOC- or Cbz-protected 5 ($R^1$=BOC or Cbz) apparently attacked the triflate even before cyclen could be added.

A satisfactory result was obtained for successful activation and coupling with cyclen with only a single inversion by using a 4-nitrobenzenesulfonate group, which was introduced within an hour using DMAP catalyst.[5] The solution of 6 so produced was then treated with excess (3 equiv) of cyclen to assure a high degree of monoalkylation. After stirring overnight, the reaction mixture was washed with large amounts of water to remove the excess cyclen. Compound 7 was isolated in a semi-crude form, suitable for the next step. The use of excess cyclen ($35 per gram in 100 g quantities) may potentially be a drawback but it may significantly simplify the purification process and increase the purity of the product as well. Additionally, cyclen may also be recovered.

The triflate of commercially available (S)-lactic acid methyl ester was made in a way which avoids its purification by distillation or column chromatography, giving almost quantitative yields without racemization.[4] Alkylation of semi-crude 7 with this triflate (3.3 equiv) in the presence of $K_2CO_3$ was complete after overnight stirring. Not all KOTf could be removed, however, even using aqueous washing of the solution of (RRRR)-8 in organic solvents. Thus, semi-purified (RRRR)-8 was converted to a salt (RRRR)-10 using HCl in methanol, which kept the four methyl ester groups intact but removed the BOC group for future coupling to a carrier, such as a dendrimer. Analysis of both (RRRR)-8 and (RRRR)-10 by $^{13}$C NMR on a 500 MHz spectrometer showed the presence of only a single set of carboxylate carbons, consistent with both diasteromeric as well as enantiomeric purity, since if any of the four chiral centers epimerized partially, more than a single set of resonances would have been seen. Similar treatment of compound 7 with methyl bromoacetate, followed by methanolic HCl, gave compound 11 of presumed (R)-configuration.

The method of the present invention provides several advantages. First, the method provides a high overall yield. Overall yields of (RRRR)-10 and (R)-11 from 4 are all greater than 70%. The method is also simple and scalable. The fact that all purifications after formation of 5 are done by extraction or precipitation speeds synthesis and makes large-scale reactions feasible.

Both precursors (RRRR)-10 and (R)-11 have been successfully linked through the free amino group to acylating agents. The tetraester salts are also stable for storage, without danger of racemization because of the protonation state of the samples—they are essentially in a buffered state.

Figure 4:
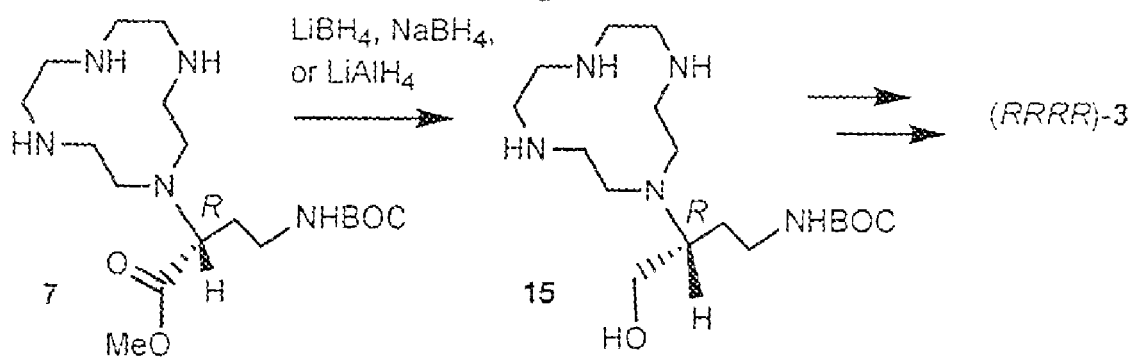
FIG. 4 is a scheme for the synthesis of HP-DO3A.

The synthesis of a fully deprotected compound (RRRR)-1 is shown in FIG. 4. Treatment of either (RRRR)-8 or (RRRR)-10 with base in methanol-water mixture led to exclusive or extensive formation of lactam 13 at the expense of (RRRR)-1, a totally unacceptable result since the side-chain amino group was now useless. However, treatment of (RRRR)-8 with a slight excess (4.5 equiv) of LiOH in THF-water led to clean hydrolysis of the methyl esters without any evidence for lactam formation. Subsequent deblocking of the side-chain Boc group proceeded without incident.

Lactam formation from 10 on basification could be a serious problem, because the free side-chain amino group would be unavailable as a linker to a carrier, such as a nanodevice. However, basification of the salt of 10 in the presence of acylating agent (e.g. DCC-activated carboxylic acid, carboxylic acid chloride, etc.) and in the absence of hydroxide (which could be the culprit in surprisingly facile removal of the BOC group during formation of 13) prevents lactam formation and ultimately leads to be attached to the desired nanodevices (schematically illustrated as 14 in FIG. 3)

The synthesis of a HP-DO3A analog 3 is illustrated in FIG. 4. In compound 7, the single ester moiety is reduced to the alcohol 15 using a reducing reagent, such as $LiBH_4$, $NaBH_4$, or $LiAlH_4$. $LiBH_4$ and $NaBH_4$ have been shown to reduce BOC- or Cbz-amino acid methyl esters without reduction of the carbamate.[6] $LiAlH_4$, under carefully controlled conditions, has been shown to function similarly.[7] Subsequent conversions of compound 15 follows those done in FIG. 2.

In anther aspect of the present invention, the analysis of intermediates and products for potentially interfering impurities is of prime importance. For example, it is desired that final products are completely free of any other primary amine besides the one desired, because any mixture of amines may lead to heterogeneous mixtures of coupling products. This may lead to complications such as a dendrimer surface with some sites unavailable to gadolinium binding, or heterogeneous populations of dendrimers with variable chemical and physical properties. The impurities may be identified by using NMR, such as 500 MHz NMR, HPLC, or LC-MS. For example, HPLC or LC-MS (Finnigan LCQ electrospray-MS) was used to detect the presence (if any) of unreacted compound 5 in semi-crude 7 or subsequent intermediates.

Potentially interfering impurities may also be synthesized if necessary and conclusively identified. For example, DMAP catalyst is present in semi-crude 7. Its fate in the subsequent step—exposure to strong alkylating agents such as the triflate or bromide—is unknown—though alkylation of pyridines in general is a common reaction. Therefore, in separate experiments, DMAP is alkylated with these agents, and the resulting products are identified using standard techniques. Finally, samples of (RRRR)-8 and (R)-10 is analyzed for these potential side-products and it needled additional purification steps may be included in their synthesis.

All compounds need to be fully characterized, including NMR, MS, HPLC, elemental analysis, and optical purity determination (e.e), such as using chiral HPLC or optical rotation.

Though the tetraester salts (RRRR)-10 and (R)-11 appear to be chemically stable for months in tightly sealed containers in desiccators, the materials were produced as extremely hygroscopic powders. Even in the relatively dry air of San Diego, the powdery material would start to become sticky within minutes of exposure to laboratory air. Absorption of water may cause chemical changes, for example hydrolysis: in fact, we have monitored samples of 10 and 11 in $CD_3OD$-$D_2O$ solutions and find after one day at 25° C. evidence for release of $CH_3OD$ from methyl ester hydrolysis. Short exposure to lab air would not be expected to lead to significant hydrolysis, but if the samples pick up water their mass changes and with it the percent composition by weight of desired chelator, which if ignored would lead to errors in stoiChiometry during attempted nanodevice construction.

To avoid all these problems, the bifunctional chelator of the present invention may be formulated into various salt forms, including, but not limited to, bromide or chloride. This can be simply achieved using HBr or HCl in methanol during the removal of the BOC group. Alternatively, the bifunctional chelator may also be packaged in standard sizes for use.

The examples set forth above are provided to give those of ordinary skill in the art with a complete disclosure and description of how to make and use the preferred embodiments of the compositions, and are not intended to limit the scope of what the inventors regard as their invention. Modifications of the above-described modes for carrying out the invention that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

The invention also provides the following compositions:

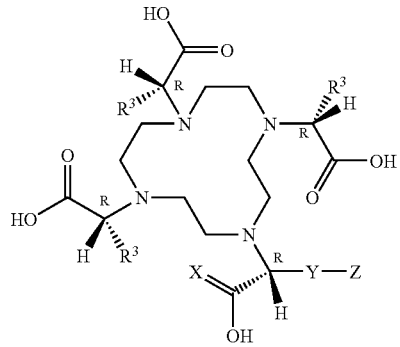

(RRRR)-1  $X = O, R^3 = CH_3$  DOTMA analog
(R)-2  $X = O, R^3 = H$  DOMA analog
(RRRR)-3  $X = H + H, R^3 = CH_3$  HP-DO3A analog Z = side chain group for coupling and dendrimer formation
Y = linking group of atoms connecting Z and rest of molecule, for example $(CH_2)_n$ where n is between 1 and 10

Z = hydroxyl (A)
Z = thiol (B)
Z = amino (C)
Z = hydrazine (D)
Z = carbonyl (E)
Z = alkene (F)
Z = alkyne (G)
Z = azide (H)

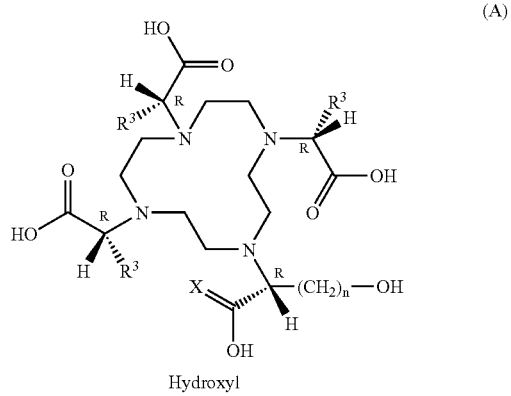

Hydroxyl

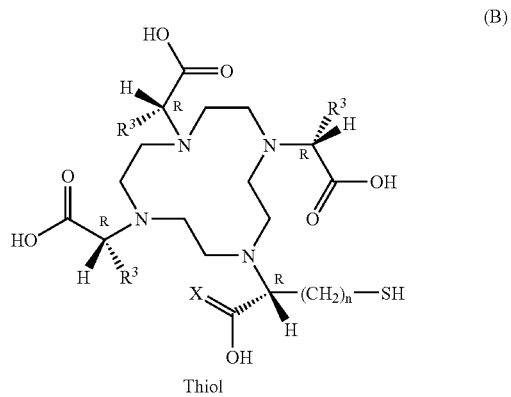

Thiol

-continued (C)
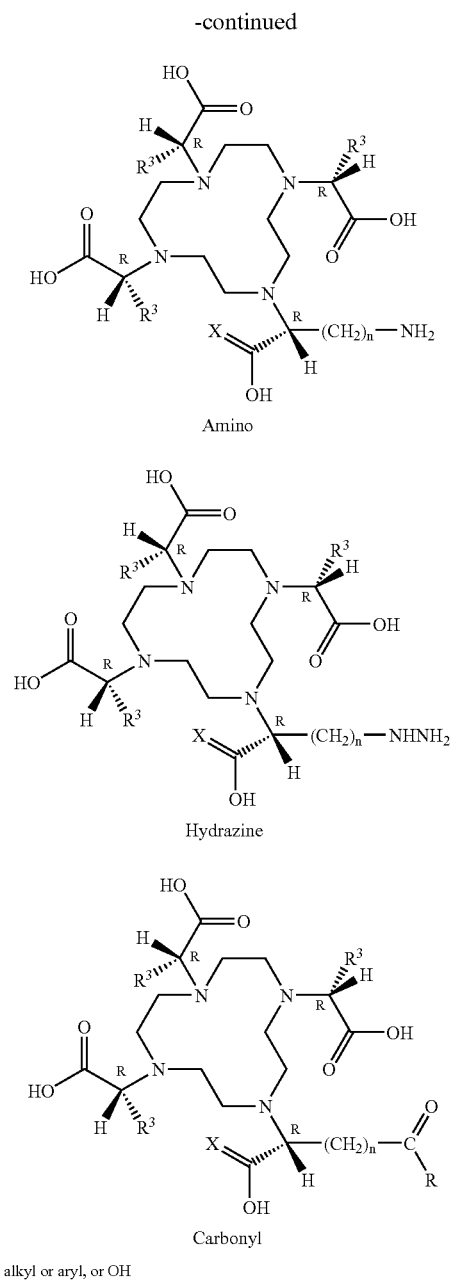

Amino

Hydrazine

Carbonyl

R = H, alkyl or aryl, or OH

Alkene (C)

(D)

(E)

(F)

-continued

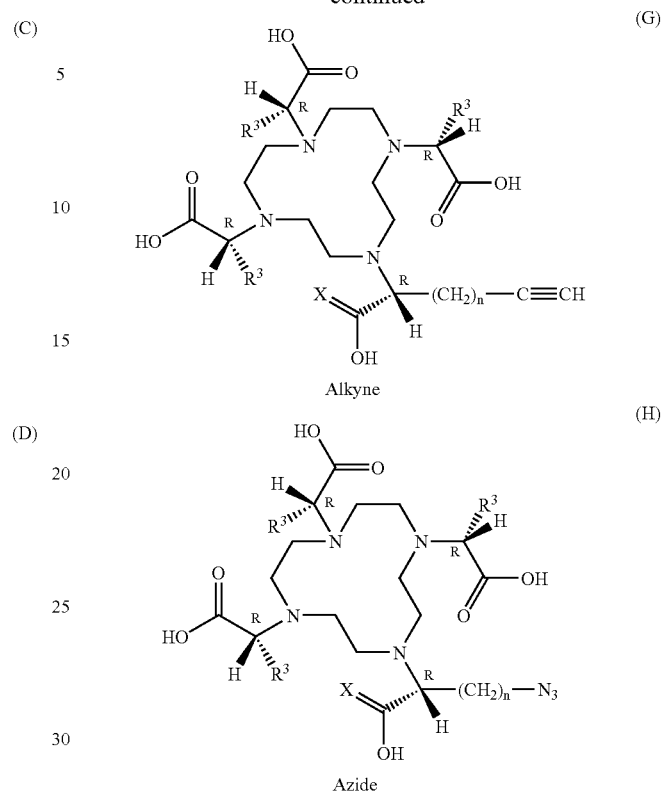

Alkyne

Azide (G)

(H)

Figure 1:
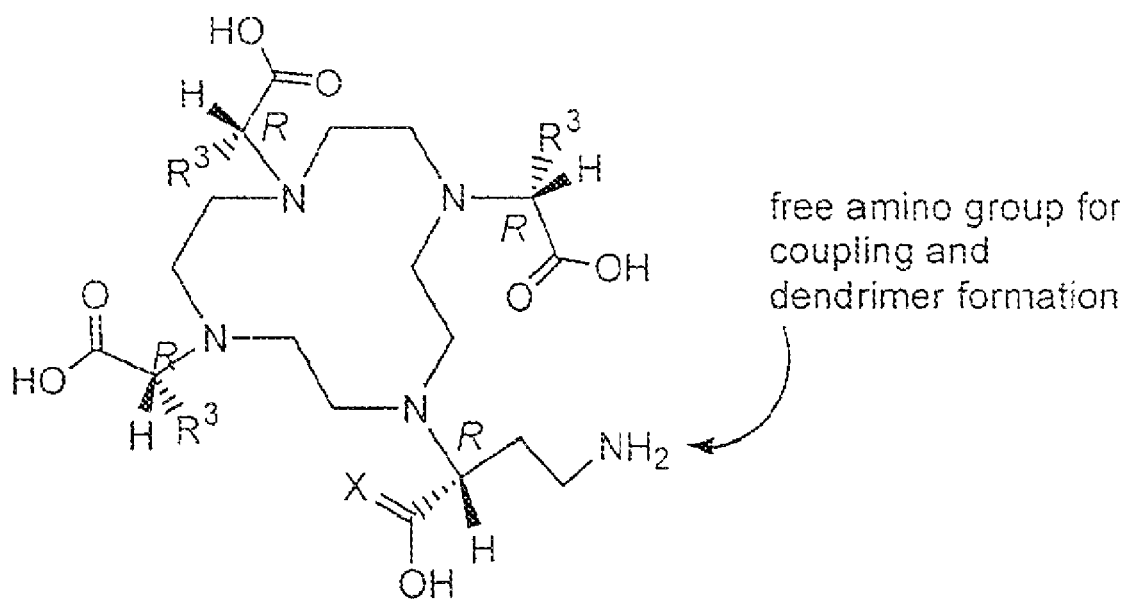
FIG. 1 shows representative examples of bifunctional chelators for lanthanides.
Figure 3:
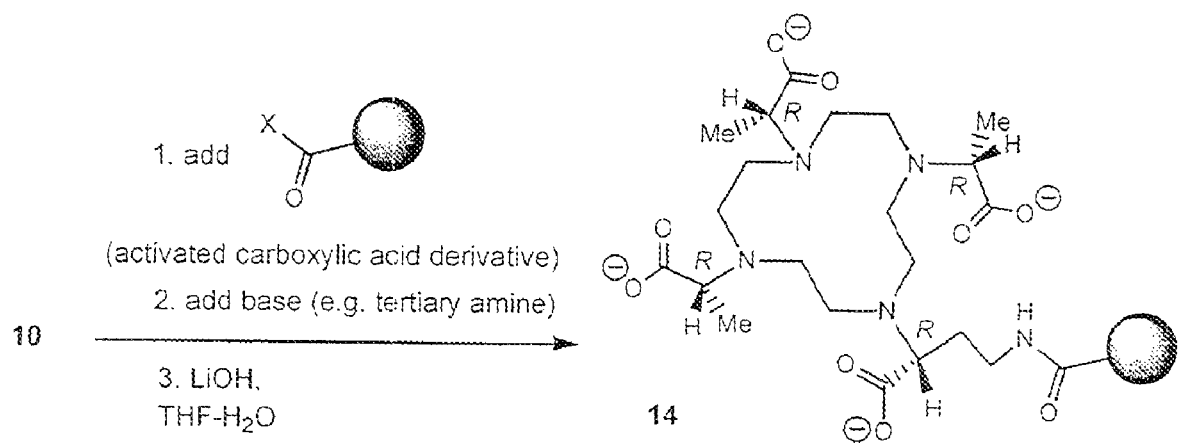
FIG. 3 illustrates the attachment chemistry for bifunctional chelators.

In alternative embodiments, a compound of the invention comprises a formula as set forth in FIG. 1, or a compound made by the synthesis method of FIG. 2 or FIG. 4, or a compound of FIG. 3.

In alternative embodiments, a compound of the invention, e.g., a bifunctional chelator of the invention, has (comprises) a chelating moiety with specific geometry and charge, and a side arm with a functional group, such as hydroxyl (A), thiol (B), amino (C), hydrazine (D), carbonyl (E), alkene (F), alkyne (G) or azide (H), for attachment to a carrier, such as dendrimers, nanoparticles, or quantum dots. Such compositions of matter comprise the structures illustrated and described herein (e.g., as shown above).

The invention provides carrier, dendrimers, nanoparticles and/or quantum dots comprising the structures illustrated and described herein.

In alternative embodiments of a compound of the invention, e.g., an imaging agent of the invention, the part of the side-chain shown as $(CH_2)_n$ may be from one to ten atoms long (n=1 to 10) and that any of the carbons may be further independently substituted. In alternative embodiments, any of the H on the Z group may be independently substituted by alkyl or aryl groups.

The compositions can be used as contrast agents in any interventional therapy; e.g., including the targeting of an undesired tissue or tissue component with high thermal energy using focused ultrasound (e.g., Cline et al., "MR Temperature Mapping of Focused Ultrasound Surgery," Mag. Resn. Med., 31:628 6136 (1994)), radiofrequency generators (e.g., Rossi et al., "Percutaneous RF Interstitial Thermal Ablation in the Treatment of Hepatic Cancer," AJR, 167:759 768 (1996)), microwave antennae (e.g., Schwarzmaier et al., "Magnetic Resonance Imaging of Microwave Induced Tissue Heating," Mag. Resn. Med., 33:729 731 (1995)), and lasers (e.g., Vogl et al., "Recurrent Nasopharyngeal Tumors: Preliminary Clinical Results with Interventional MR Imaging-Controlled Laser-Induced Thermotherapy," Radiology, 196: 725 733(1995)); the use of cryoablation (i.e., liquid nitrogen) and the injection of denaturing liquids (e.g., ethanol, hot saline) directly into the undesired tissue (e.g., Nagel et al., "Contrast-Enhanced MR Imaging of Hepatic Lesions Treated with Percutaneous Ethanol Ablation Therapy," Radiology, 189:265 270 (1993) and Honda et al., "Percutaneous Hot Saline Injection Therapy for Hepatic Tumors: An Alternative to Percutaneous Ethanol Injection Therapy," Radiology, 190: 53 57 (1994)); the injection of chemotherapeutic and/or chaotropic agents into the tissue (e.g., Pauser et al., "Evaluation of Efficient Chemoembolization Mixtures by Magnetic Resonance Imaging of Therapy Monitoring: An Experimental Study on the VX2 Tumor in the Rabbit Liver," Cancer Res., 56:1863 67 (1996)); and photodynamic therapies, wherein a cytotoxic agent is activated in vivo by irradiation with light (e.g., Dodd et al., "MRI Monitoring of the Effects of Photodynamic Therapy on Prostate Tumors," Proc. Soc'v Mag. Resn., 3:1368, ISSN 1065 9889 (Aug. 19 25, 1995)). The shared goal of all such interventional therapies is the treatment of undesirable tissue or tissue component (i.e., cancerous, tumor, neoplastic tissue or tissue component) by causing the necrosis, ablation, coagulation, or denaturation of such tissue; or, e.g., as described in U.S. Pat. No. 7,175,829.

The details of one or more embodiments of the invention are set forth in the accompanying drawings and this description. Other features, objects, and advantages of the invention will be apparent from the description and drawings, and from the claims.

All publications, patents, patent applications, GenBank sequences and ATCC deposits, cited herein are hereby expressly incorporated by reference for all purposes.

REFERENCES

1. Renn, O. and Meares, C. F. "Large-Scale Synthesis of the Bifunctional Chelating Agent 2-(p-Nitrobenzyl)-1,4,7,10-tetraazacyclododecane-N,N',N'',N'''-tetraacetic Acid, and the Determination of Its Enantiomeric Purity by Chiral Chromatography," Bioconjugate Chem. (1992) 3, 563-569.
2. Chappell, L. L., Rogers, B. E., Khazaeli, M. B., Mayo, M. S., Buchsbaum, D. J. and Brechbiel, M. W. "Improved Synthesis of the Bifunctional Chelating Agent 1,4,7,10-Tetraaza-N-(1-carboxy-3-(4-nitrophenyl)propyl)-N',N'',N'''-tris(acetic acid)cyclododecane (PA-DOTA)," Bioorg. Med. Chem. (1999) 7, 2313-2320.
3. Woods, M., Aime, S., Botta, M., Howard, J. A. K., Moloney, J. M., Navet, M., Parker, D., Port, M. and Rousseaux, O. "Correlation of Water Exchange Rate with Isomeric Composition in Diastereoisomeric Gadolinium Complexes of Tetra(carboxyethyl)dota and Related Macrocyclic Ligands," J. Am. Chem. Soc. (2000) 122, 9781-9792.
4. Effenberger, F., Burkard, U. and Willfahrt, J. "Enantioselektive Synthese N-substituierter □-Aminocarbonsäuren aus □-Hydroxycarbonsäuren," Liebigs Ann. Chem. (1986) 314-333.
5. Hoffman, R. V. and Kim, H.-O. "Preparation of (R)-2-Azidoesters from 2-((p-Nitrobenzene)sulfonyl)oxy Esters and Their Use as Protected Amino Acid Equivalents for the Synthesis of Di- and Tripeptides Containing D-Amino Acid Constituents," Tetrahedron (1992) 48, 3007-3020.
6. Salituro, F. G., Agarwal, N., Hofmann T. and Rich, D. H. "Inhibition of aspartic proteinases by peptides containing lysine and ornithine side-chain analogs of statine," J. Med. Chem. (1987) 30, 286-295.
7. Namba, K., Shinada, T., Teramoto, T. and Ohfune, Y. "Total Synthesis and Absolute Structure of Manzacidin A and C," J. Am. Chem. Soc. (2000) 122, 10708-10709.

What is claimed is:

1. A compound having a formula

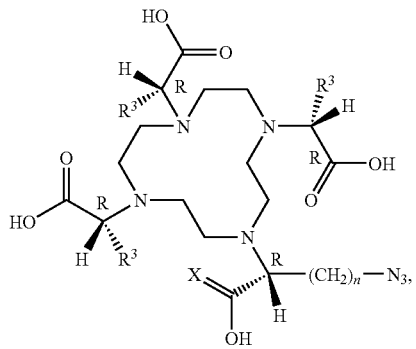

wherein $N_3$ is an azide; in the $(CH_2)_n$ linking group n is an integer between 2 and 10; and X is selected from the group consisting of O and H+H.
2. The compound of claim 1, wherein
(a) any of the H on the Y or Z group is substituted with an $R_1$ group independently selected from the group consisting of hydrogen, halo, hydroxy (—OH), thiol (—SH), cyano (—CN), formyl (—CHO), alkyl, aryl, haloalkyl, alkenyl, alkynyl, amino, nitro (—NO₂), alkoxy, haloalkoxy, thioalkoxy, alkanoyl, haloalkanoyl and carbonylox, or
(b) the $R_3$ group is substituted with an $R_1$ group independently selected from the group consisting of hydrogen, halo, hydroxy (—OH), thiol (—SH), cyano (—CN), formyl (—CHO), alkyl, aryl, haloalkyl, alkenyl, alkynyl, amino, nitro (—NO₂), alkoxy, haloalkoxy, thioalkoxy, alkanoyl, haloalkanoyl and carbonyloxy.

* * * * *